US011162596B1

(12) United States Patent
Davis

(10) Patent No.: US 11,162,596 B1
(45) Date of Patent: Nov. 2, 2021

(54) APPARATUS AND METHOD FOR INFLATING, SEALING AND DEFLATING AN INFLATABLE BODY

(71) Applicant: Margaret Denise Davis, Seattle, WA (US)

(72) Inventor: Margaret Denise Davis, Seattle, WA (US)

(*) Notice: Subject to any disclaimer, the term of this patent is extended or adjusted under 35 U.S.C. 154(b) by 286 days.

(21) Appl. No.: 16/501,874

(22) Filed: Jun. 22, 2019

Related U.S. Application Data

(60) Provisional application No. 62/763,866, filed on Jul. 5, 2018.

(51) Int. Cl.
| *F16K 31/44* | (2006.01) |
| *A63H 27/10* | (2006.01) |
| *F16K 7/10* | (2006.01) |
| *A61M 25/10* | (2013.01) |
| *B64B 1/40* | (2006.01) |
| *B64B 1/64* | (2006.01) |
| *A47C 27/08* | (2006.01) |

(52) U.S. Cl.
CPC ......... *F16K 7/10* (2013.01); *A61M 25/10186* (2013.11); *F16K 31/44* (2013.01); *A47C 27/081* (2013.01); *A63H 27/10* (2013.01); *A63H 2027/1033* (2013.01); *B64B 1/40* (2013.01); *B64B 1/64* (2013.01)

(58) Field of Classification Search
CPC .. A63H 27/10; A63H 2027/1033; F16K 7/10; F16K 31/44; A61M 25/10186; A47C 27/081
See application file for complete search history.

(56) References Cited

U.S. PATENT DOCUMENTS

| 1,426,646 | A | * | 8/1922 | Hughey | A63H 27/10 446/186 |
| 3,161,998 | A | * | 12/1964 | Lennox | A63H 27/10 141/313 |
| 4,142,322 | A | * | 3/1979 | Zeyra | A63H 27/10 446/224 |
| 4,167,204 | A | * | 9/1979 | Zeyra | A63B 41/12 137/231 |
| 4,248,008 | A | * | 2/1981 | Pitkanen | A63H 27/10 446/187 |
| 4,911,674 | A | * | 3/1990 | Cole | A63H 27/10 137/853 |
| 4,955,412 | A | * | 9/1990 | Younts | A63H 27/10 141/10 |
| 5,016,428 | A | | 5/1991 | Helling | |
| 5,105,364 | A | | 4/1992 | Kubiatowicz | |

(Continued)

*Primary Examiner* — Christopher R Harmon

(57) ABSTRACT

Apparatus and method of inflating, sealing and deflating an inflatable body including a support structure with an opening, a piece with a hole from one end to the other end, the inflatable body is secured to the support structure with an opening and the piece with a hole from one end to the other end, and the piece with a hole from one end to the other end is secured to the support structure with an opening creating an air passageway channel to inflate, seal and deflate an inflatable body. The apparatus and method can be used to inflate, seal and deflate an inflatable body when the neck or opening portion of the inflatable body is inaccessible or unexposed as well as when the neck or opening portion of the inflatable body is accessible and exposed.

13 Claims, 4 Drawing Sheets

(56) References Cited

U.S. PATENT DOCUMENTS

Figure 1:
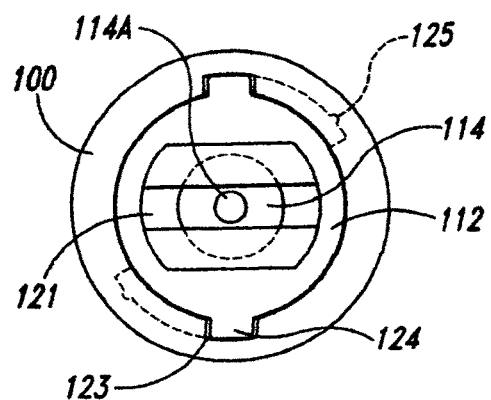

| | | | |
|---|---|---|---|
| 5,121,595 A * | 6/1992 | Shore | A63H 27/10 |
| | | | 141/173 |
| 5,595,521 A | 1/1997 | Becker | |
| 7,195,029 B2 | 3/2007 | Wass | |
| 8,349,417 B2 | 1/2013 | Heffernan | |
| 9,011,195 B2 | 4/2015 | Sidwell | |
| 9,027,877 B1 | 5/2015 | Brookes | |
| 9,688,370 B1 | 6/2017 | Shiue | |
| 9,844,737 B1 | 12/2017 | Warner et al. | |
| 10,228,067 B2 | 3/2019 | Miller | |
| 2009/0084892 A1 | 4/2009 | Nguyen et al. | |
| 2016/0243454 A1 * | 8/2016 | Laden | A63H 27/10 |

* cited by examiner

APPARATUS AND METHOD FOR INFLATING, SEALING AND DEFLATING AN INFLATABLE BODY

CROSS-REFERENCE TO RELATED APPLICATIONS

This application claims the benefit of provisional patent application Ser. No. 62/763,866 filed Jul. 5, 2018 by the present inventor.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

STATEMENT REGARDING FEDERAL SPONSORED RESEARCH AND DEVELOPMENT

Not Applicable

STATEMENT REGARDING PRIOR DISCLOSURES BY THE INVENTOR OR A JOINT INVENTOR

Not Applicable

BACKGROUND OF THE INVENTION

References in prior art providing ways of inflating, sealing, and deflating a balloon or inflatable body include various approaches. Inflatable balloons and other inflatable bodies are normally inflated injecting some form of air or gas either orally, manually or by machine directly into the neck or opening portion of the inflatable body and then the balloon or other inflatable body's neck is tied in a knot, or tied with string, or pressed together to create a seal, or stretched over another article to create a seal or plugged or capped to seal. Some of the prior art provided ways of inflating inflatables that are expensive to make and are not versatile, are complicated and time consuming to use, are highly technical, that are very heavy for consumer products and products that do not need a highly technical or expensive solution. References in prior art that do not provide a synergistic solution but need many parts and pieces to do all the inflation, sealing and deflation processes required on an inflatable body.

The problem of how to get air into the balloon or other inflatable body quickly and easily if the neck or opening portion is not directly accessible to do any of the above because the balloon or inflatable body is part of a decorative design, assembled product or other applications where the neck or opening portion can not be manipulated directly because it is unexposed or inaccessible.

The problem of how to adjust the inflatable body's size and shape easily and quickly if the neck or opening portion is not directly accessible because the balloon or inflatable body is part of a decorative design, assembled product or other applications where the neck or opening portion can not be manipulated directly because it is unexposed or inacessible but the size and shape have to be adjusted in order to make the product or application look as intended or work as intended.

The problem of a quick, easy and economical way to inflate, adjust, seal and deflate a balloon or inflatable body that will allow for better control of the inflation and deflation process. There are those people who are using helium, hot air balloons and solar balloons as a means to make personal air flights possible in small baskets, chairs, and other craft. Some of these people are popping helium filled balloons in order to make the craft descend.

FIELD OF INVENTION

Not Applicable

PRIOR ART

| | | |
|---|---|---|
| U.S. Pat. No. 9,688,370 B1 | Jun. 27, 2017 | Shiue; Jeff Heng-Wen |
| U.S. Pat. No. 9,011,195 B2 | Apr. 21, 2015 | Paul E. Sidwell |
| U.S. Pat. No. 8,349,417 | Jan. 8, 2013 | Heffernan |
| U.S. Pat. No. 10,228,067 | Mar. 12, 2019 | Miller; Steven Earl |
| U.S. Pat. No. 7,195,029 B2 | Mar. 27, 2009 | Lloyd G. Wass |
| US 20090084892 | Apr. 2, 2009 | Nguyen; Phu; Nguyen; Logan A. |
| U.S. Pat. No. 5,105,364 | Apr. 7, 1992 | Kubiatowicz |
| U.S. Pat. No. 9,844,737 | Dec. 19, 2017 | Wesley Warner, Troy Stark |
| US 00595521A | Jan. 21, 1997 | Charles R. Becker |
| U.S. Pat. No. 9,027,877 B1 | May 12, 2015 | Kyle Brookes |
| U.S. Pat. No. 5,016,428 | May 21, 1991 | Helling; Robert W. |

BRIEF SUMMARY OF THE INVENTION

This present invention is an apparatus invented to overcome the disadvantages of prior art for inflating, adjusting, sealing and deflating a balloon or inflatable body, particularly in areas of product design, assembled products or applications where the balloon or inflatable body's neck or opening portion is inaccessible or unexposed.

Tying a balloon or inflatable body in a knot after inflation is cumbersome, slow and inefficient especially when the inflatable material is thick. Self-sealing options, plugs, caps, and stretching the inflatable body limits design options and do not provide a synergistic process.

This present invention is the discovery of an apparatus that will allow for quick and easy inflation, sealing, deflation and adjustment of the size and shape of balloons and other inflatable bodies that are part of product designs, assembled products, and other inflatable body applications where the neck or opening portion of the inflatable body is not accessible or is unexposed. When too much air or other inflation gases are injected into a balloon or inflatable body this present invention will allow it to be released quickly and easily so that the shape and size of a balloon or inflatable body is easily controlled and corrected as needed. This process can be reversed when there is too little air injected so that the balloon or inflatable body's size and shape can be easily adjusted.

This present apparatus can also be used when the neck or opening portion of the balloon or other inflatable body is accessible and is exposed using the same concept. This present invention can be used as a means to re-inflate balloons and other inflatables that have deflated due to the air escaping. Generally balloons that are tied in a knot are not re-inflated. This present apparatus will allow for re-inflation of a deflated balloon or inflatable body and increase reuse of these products.

Some of the objectives of this present invention is to allow the quick, easy and economical inflation, sealing, deflation and adjustment of more configurations, designs and types of inflatable bodies to increase design freedom, but specifically those balloons and other inflatable bodies that are part of product designs, assembled products, and other applications where the neck or opening portion of the inflatable body is not accessible or is unexposed when there is a need to inflate the inflatable body.

BRIEF DESCRIPTION OF THE SEVERAL VIEWS OF THE DRAWING(S)

Figure 3:
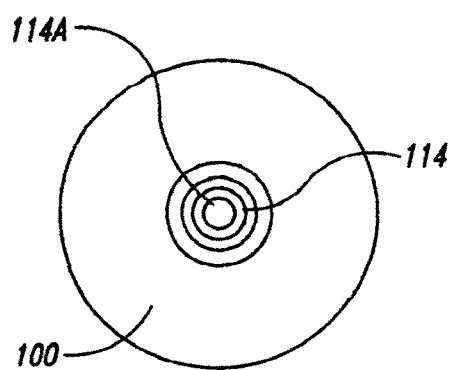
Figure 2:
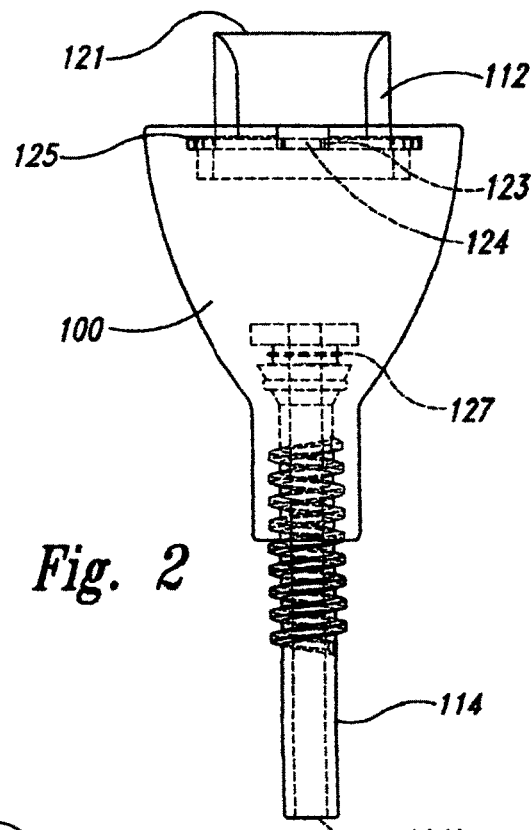
Figure 4:
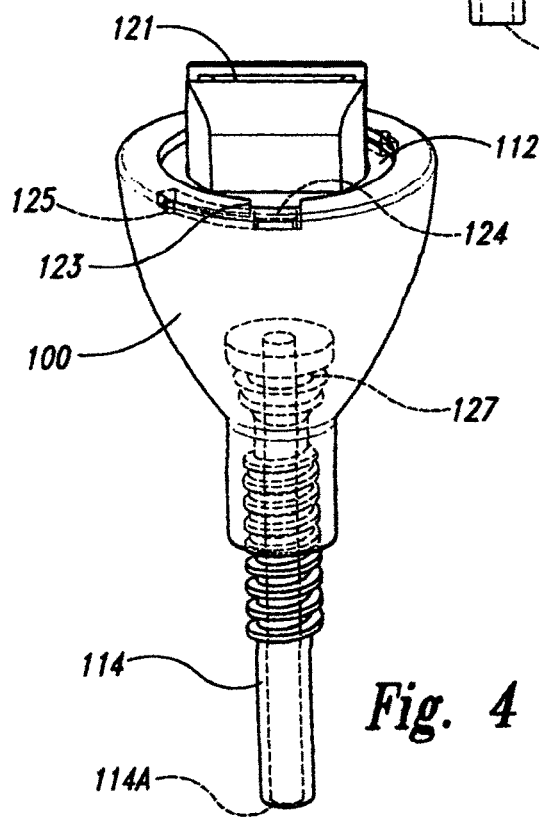
Figure 5:
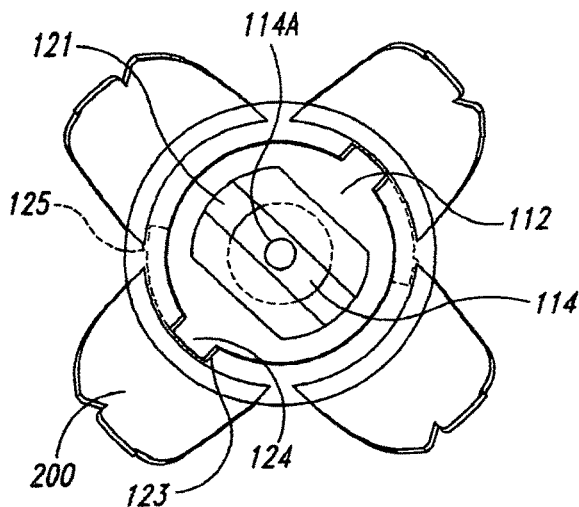
Figure 6:
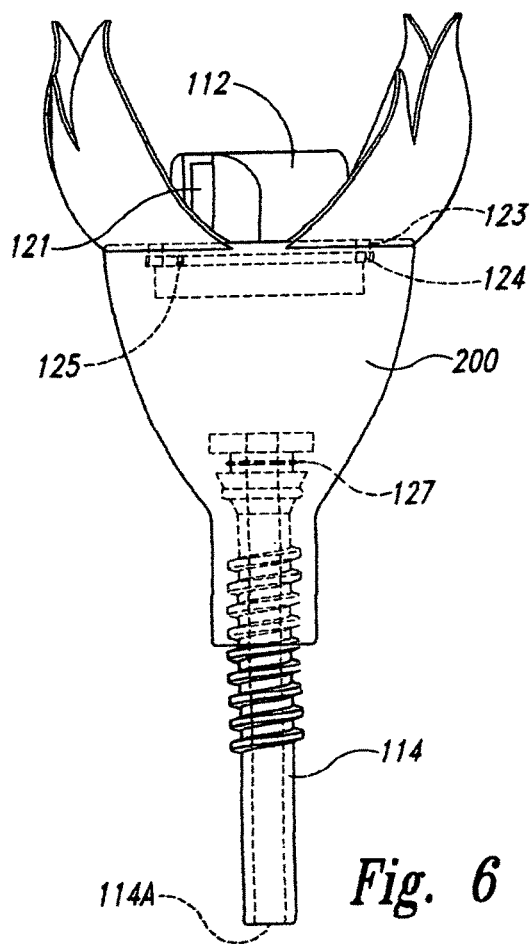
Figure 7:
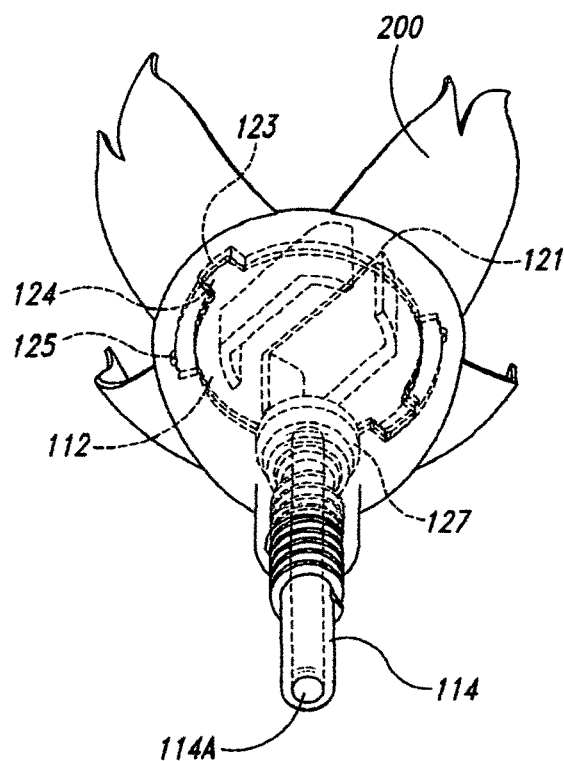
Figure 8:
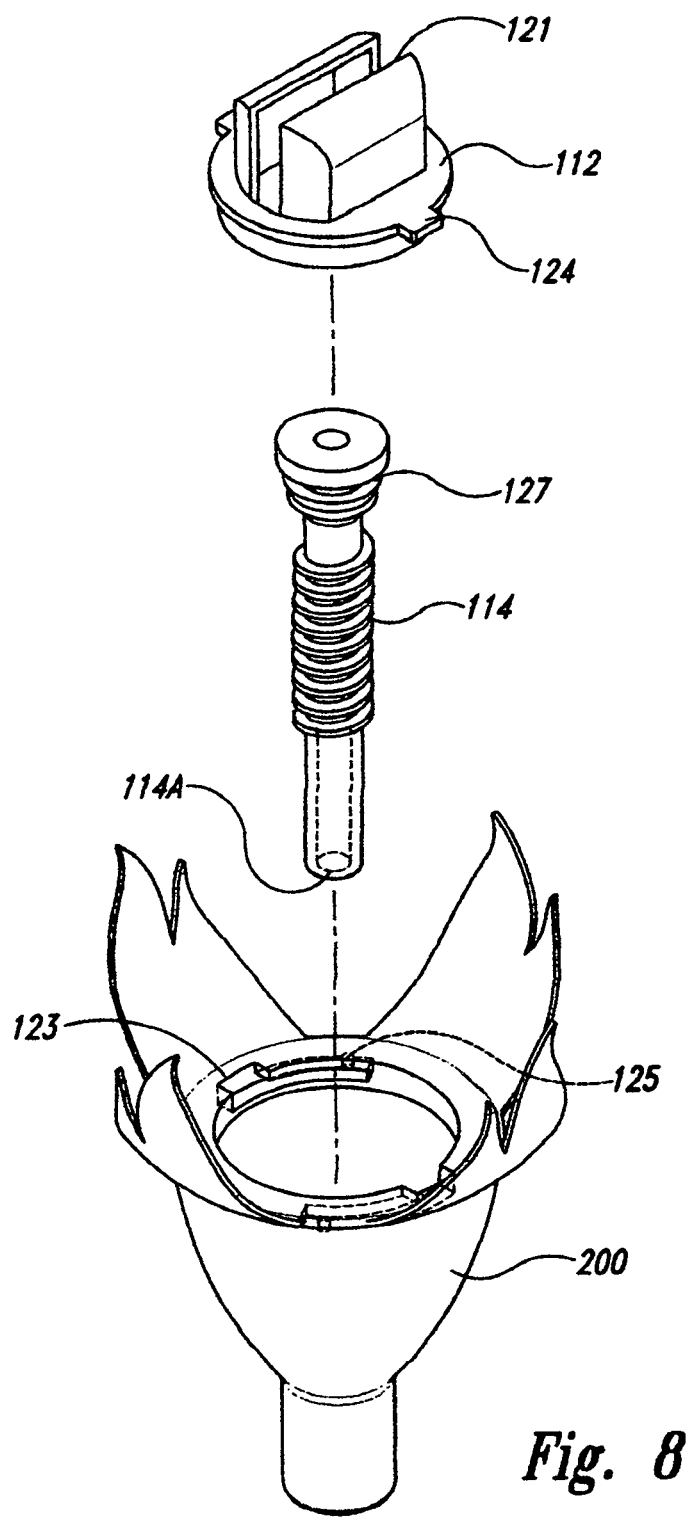
Figure 9:
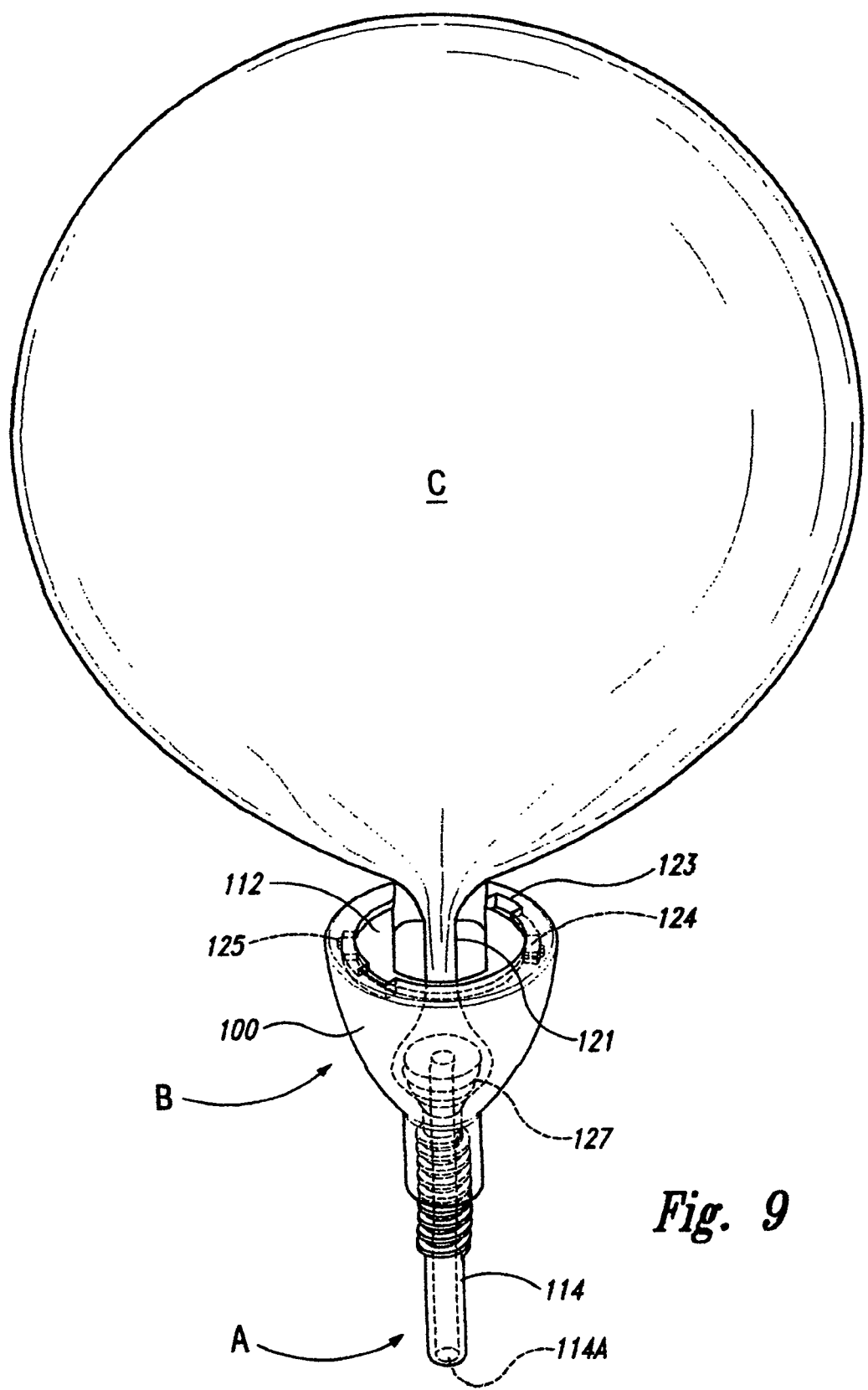

FIG. 1 is a top view of the first embodiment of the apparatus for inflating, sealing and deflating an inflatable body FIG. 2 is a side view of the first embodiment of the apparatus for inflating, sealing and deflating an inflatable body FIG. 3 is a bottom view of the first embodiment of the apparatus for inflating, sealing and deflating an inflatable body FIG. 4 is a side perspective view of the first embodiment of the apparatus for inflating, sealing and deflating an inflatable body FIG. 5 is a top view of the second embodiment of the apparatus for inflating, sealing and deflating an inflatable body FIG. 6 is a side view of the second embodiment of the apparatus for inflating, sealing and deflating an inflatable body FIG. 7 is a bottom perspective view of the second embodiment of the apparatus for inflating, sealing and deflating an inflatable body FIG. 8 is a exploded perspective view of the second embodiment of the apparatus for inflating, sealing and deflating an inflatable body FIG. 9 is a side view of the first embodiment of the apparatus for inflating, sealing FIG. 9 (continued) and deflating an inflatable body assembled to a latex balloon

DETAILED DESCRIPTION OF THE INVENTION

Reference Numeral List

100—Main body of the first embodiment
112—Insert disc
114—Stem
114a—Hole for air passageway channel
121—Insert disc center cutout
123—Cutout at the top section of main body
124—Outside pins section of insert disc
125—Inside pins part of main body
127—Tightened wire, annulus or another form of attachment
200—Main body of second embodiment
A—Means for air injection
B—Inflatable body twist, interlace, and stretch area
C—Balloon or other inflatable body to be inflated

DETAILED DESCRIPTION OF INVENTION

Referring to the drawings of the apparatus for inflating, sealing and deflating an inflatable body. FIG. 1 shows a top view of the first embodiment of the apparatus. In this embodiment the apparatus has a main body 100 that can be a rounded shape as shown or another designed shape depending on the application. The insert disc 112 allows an inflatable body's neck or opening portion to be inserted through the center of the insert disc's 121 cut-out and to be mounted securely around the top section of the stem 114 in a way that makes sure the openings of both the inflatable body and the hole in the stem 114 are unobstructed to allow for air to flow between the two. The insert disc 112 can be attached to the main body 100 by inserting and turning the insert disc 112 until the outside pins 124 falls between the inside pins 125 and locks in place.

FIG. 2 shows a side view of the first embodiment of the apparatus. The view shows the insert disc 112 with pins 124 inserted into the top of the main body 100 as well as the cutouts 123 on the top section of the main body which allows the disc 112 to be inserted and secured using inside pins 125. Showing the cut-out 121 where the neck or opening portion will be inserted and the tightened wire 127 where the inflatable body's neck or opening portion will be secured around the top of stem 114. The stem 114 is inserted inside the main body 100 and the top part of the stem's 114 male threads are mated with the female threads in the lower part of the main body 100 and the stem 114 protrudes from the bottom of the main body allowing the stem 114 to be turned in one direction to seal the inflatable body and reversed in the other direction to deflate the inflatable body after inflation. The hole in the stem 114 will be used as an airway at entry point 114a. After the stem's 114 outside male threads have been inserted into the main body's 100 lower section and partially mated with the female threads to secure the stem 114, the insert disc 112 can be attached to the main body 100 by inserting and turning the insert disc 112 until the outside pins 124 falls between the inside pins 125 and locks in place. This assembly creates an air passageway channel that can be used to inflate the inflatable body when air is injected into the hole 114a, this assembly will also allow an inflatable body to be sealed by turning the stem in one direction to twist, interlace and stretch the inflatable body together, keeping the air from escaping the inflatable body, this assembly will also allow an inflatable body to be deflated by turning the stem 114 in the opposite direction to un-twist, un-interlace and un-stretch the inflatable body, allowing the air to escape the inflatable body.

FIG. 3 shows a bottom view of the first embodiment's main body 100. The hole 114A in the stem 114 allows air or inflation gases to enter the inflatable body's air passageway channel.

FIG. 4 shows a side perspective view of the first embodiment of the apparatus. FIG. 4 shows the insert disc 112 with outside pins 124 inserted into the top of the main body 100 as well as the cutouts 123 on the top section of the main body 100 which allows the disc 112 to be inserted and using pins 124, secured between inside pins 125. FIG. 4 shows the cutout 121 where the neck or opening portion of the inflatable body will be inserted and the wire 127 or other form of attachment, where it will be securely tightened around the top of stem 114. The stem 114 is inserted inside the main body 100 and the top part of the stem's 114 male threads are mated with the female threads in the lower part of the main body 100, the stem 114 protrudes from the bottom of the main body allowing the stem 114 to be turned in one direction to seal the inflatable body and reversed in the other direction to deflate the inflatable body. The hole in the stem 114 will be used as an airway at entry point 114a.

FIG. 5 shows a top view of the second embodiment of the apparatus. The main body 200 is an alternative configuration with a decorative design. The inside disc 112 with attached outside pins 124 and cutout 121 is inserted and can be secured at the top of the main body 200 using the cutouts 123 and inside pins 125, this stability allows the inflatable body's neck or opening portion after it has been attached, to be used as part of the air passageway channel after air has been introduced through the hole 114 at 114A.

FIG. 6 shows a side view of the second embodiment 200 of the apparatus for inflating, seal and deflating an inflatable body. The inside disc 112 with attached outside pins 124 and cutout 121, is inserted and can be secured at the top of the main body 200 using the cutouts 123 and inside pins 125, this stability allows the inflatable body's neck or opening portion after it has been attached to the top of stem 114 using wire 127 or another form of attachment to be used as part of the air passageway channel after air has been introduced through the hole 114 at 114A.

FIG. 7 shows a bottom perspective view of the second embodiment 200 of the apparatus. The stem 114 is secured using the top part of the stem's 114 male threads mated with the female threads inside the lower part of the main body 200 protruding through the bottom of the main body 200. The stem's 114 hole at the air entry way 114A is used to inject air into the inflatable body. At the top of FIG. 7, the inside disc 112 with attached outside pins 124 and cut-out 121 is inserted and can be secured at the top of the main body 200 by inserting it using the cut-outs 123 and sliding it between the inside pins 125 to secure it, this stability allows the inflatable body's neck or opening portion after it has been attached to the stem 114 using wire 127 or another form of attachment, to be used as part of the air passageway channel after air has been introduced through the hole 114 at 114A.

FIG. 8 shows a disassembled exploded perspective side view of the apparatus using the second embodiment. The perspective side view of the main body 200 and the prespective side view of the insert disc 112 shown above with 121 outside pins attached to the disc and used for securing the insert disc when inserted into the cutouts 123 to slide in place between the inside pins 125, and shown above the main body 200 as a perspective side view of the stem 114 with hole 114a shown above the main body with the wire 127 or other way to secure inflatable body's neck or opening portion used to tighten an inflatable body's neck or opening portion at 127 to the top of stem 114. This view is showing a disassembled view of the apparatus and how the apparatus's parts all fit together and are assembled in order to allow for the inflation, sealing and deflation process to occur.

FIG. 9 shows a side view of the first embodiment of the apparatus with an inflatable body, a latex balloon, shown as C attached. FIG. 9 shows the insert disc 112 inserted into the top of the main body 100 of the first embodiment by using the 123 main body cutouts and the insert disc outside pins 124 and secured to the main body 100 using the inside pins 125. FIG. 9 shows the neck of the balloon C threaded through the insert disc's 112 center cutout 121 and placed over the top ridge of the stem 114 where it is attached with a wire 127 tighten to secure it, creating an air passageway channel. The area between the insert disc center cutout 121, where the latex balloon C, is threaded through and secured on top of the stem 114 is where the inflatable body's twist, interlace and stretch area B is located. Area B allows the latex balloon C or other inflatable body to be twisted, interlaced and stretched together keeping the air injected by a means of air injection A using the hole in the air passage way channel 114A from escaping and sealing the balloon or other inflatable body when the stem 114 is turned in one direction. Twist area B also allows the latex balloon or other inflatable body to be un-twisted, un-interlaced and un-stretched together in order to release the injected air and deflate the latex balloon or other inflatable body when the stem 114 is turned in the opposite direction.

Alternative Embodiments

An alternative embodiment not shown would allow an inflatable body with two necks or opening portions, one on the outside and one on the inside, to be inflated by anchoring with a knot or another from of anchoring, the inside neck or opening portion of the inflatable body to the inside of the disk 112 using cutout 121 and following all the other instructions indicated above.

Operation of Invention

Mode of application and operation for using the first and second embodiments of the apparatus for inflating, sealing and deflating an inflatable body.

Step 1. Both the insert disc 112 and the stem 114 must be detached from the main body 100 or 200 in order to mount the inflatable body on them.

Step 2. The inflatable body's neck or opening portion is inserted or threaded through the insert disc using the disc's center cut-out 121.

Step 3. The inflatable body's neck or opening portion is pulled over and around the stem's 114 top ridge and attached to the stem 114 using wire 127 or another means of attaching it securely, unobstructing the airway path between the neck or opening portion and the hole in the stem 114 yet attaching it as air-tight as possible. The inflatable body will now have the insert disc 112 and the stem 114 attached to it. This will allow the inflatable body to be inflated after it is inserted into the main body 100 or 200.

Step 4. The inflatable body with the insert disc 112 and the stem 114 attached to it, are inserted into the inside cavity of the main body 100 or 200. This configuration in inserted by first putting the end of stem 114's outside threads into the center of the main body 100 or 200 until it reaches the opening in the lower section, and by inserting and turning the stem 114 until a portion of the male threads are visible and protruding through the end of the main body 100 or 200. Mating the male threads on the outside of the stem 114 with the female threads on the inside of the lower section of the main body 100 or 200 will secure the stem 114 to the lower section of the main body 100 or 200 and will allow the inflatable body to be twisted, stretched and interlaced together creating a seal in area B in FIG. 9.

Step 5. Then insert the insert disc 112 into the top portion of the main body 100 or 200 by aligning the outside pins 124 with the cutouts 123 at the top of the main body 100 or 200.

Step 6. After the insert disc 112 has been inserted, turn it until it settles into the space between the inside 125 pins at the top of the main body 100 or 200. This allows the inflatable body to be secured for inflation.

Step 7. Next introduce air using the stem 114 by a means of air injection A as shown in FIG. 9 using the hole at air entry way 114a. Air will travel through the hole and up to the inflatable body and inflate it.

Step 8. After the amount of air desired has entered the inflatable body, keep the air from escaping by turning the stem 114 in one direction until it stops and can no longer be turned.

Step 9. If you would like to deflate the inflatable body, reverse step 8 and turn the stem 114 in the opposite direction to allow the air to escape.

Advantages

1. This apparatus for inflating, sealing and deflating inflatable bodies is versatile, can be used with all kinds of inflatables made with all kinds of materials including but not limited to latex, mylar, nylon, plastics, cloth, paper and more and for all types of purposes and designs.

2. This apparatus has more than one function when using on an inflatable body, it has the capacity to inflate, seal and deflate the inflatable body. It is synergistically able to control the shape of an inflatable body that requires specific sizing or shaping. This apparatus will allow adjusting the air inflation process as necessary without the need for additional steps, processes or equipment.

3. This apparatus is economical to manufacture because it has very few parts it uses part of the inflatable body's own material as part of the air passageway channel.

4. It is versatile and can be made in many different sizes, materials, colors and designs.

5. This apparatus makes the inflation, sealing and deflation process easier, faster and more convenient and less cumbersome for the person trying to inflate, seal or deflate an inflatable body because there will be no need to tie it in a knot, tie it with a string, rubber band, etc.

6. Thicker balloons and inflatable bodies that are hard to tie can be inflated with this apparatus. Inflatable bodies where the neck or open portion is larger than regular sizes and be inflated with this adjustable apparatus.

7. Balloons and inflatable bodies with more complicated configurations and designs with more than one neck or opening portion can be inflated using this apparatus.

8. The ability of the apparatus to inflate, seal and deflate an inflatable body will allow for more control of the inflatable body's shape because if too much air has been injected, air can be quickly and easily released to control the size and shape of the inflatables.

9. This apparatus can be made of all types of materials including but not limited to plastics, metals, wood and may include all types materials and kinds of designs to secure attachments including adhesives, glues, metal straps, wire and rings. The apparatus can be designed in all types of colors and styles to accommodate the application it is used for. The apparatus can be designed and manufactured in all types of sizes and dimensions to accommodate the application it is used for.

10. This apparatus can be made with alternative designs that combine some of the parts, for example the insert disc can be made as part of the support structure with an opening in some applications. Other alternative designs can combine the pieces and configurations other than the two embodiments in this document are possible with this apparatus.

11. This apparatus encourages re-use of inflatable bodies that were used once and thrown away because they had been tied in a knot or another way that did not allow re-use. This apparatus allows a deflated inflatable body to be re-inflated by reversing the steps.

12. This apparatus can be used when the neck or opening portion of the inflatable body is inaccessible or unexposed because it is part of a design that requires it to be hidden and only a portion or portions of the inflatable body needs to be visible.

RAMIFICATIONS AND SCOPE

This apparatus is a way to inflate helium balloons for balloon flights and will allow better air control. Hot air balloon flights may also benefit because people are injured and killed in commercial balloon flights and the typical hot air balloon flight uses a process in which a fire burner is used to heat the air allowing the balloon to rise from the thinner air created. However the process can be dangerous because air makes fire more combustible and having a burner on board a hot air balloon increases the danger.

Other uses for this apparatus include for inflating, sealing, deflating and controlling weather balloons, solar balloons, areostats, blimps, dirigibles, medical balloons, balloon catheters, medical devices, airships, toy balloons, balloon flowers, balloon decorative designs, rubber hoses and pipes, air mattresses, flexible bodies and drones.

There are non-inflation uses for this apparatus in medical, industrial and commercial applications using liquids as well as gases.

I claim:

1. An apparatus for inflating, sealing, and deflating an inflatable body comprising:
    a support structure comprising a main body and an opening;
    a stem comprising a top end, a bottom end, and a hole from the top end to the bottom end; and
    a means of securing an inflatable body to the support structure, comprising a means of securing the inflatable body to the stem and a means of securing the stem to the support structure, wherein the means for securing the inflatable body to the stem comprises a tighten wire, adhesive, glue, strap, or annulus;
wherein the stem is configured to inflate the inflatable body when the stem is injected with air or other gases, and further wherein turning the stem in a first direction will stop the air from escaping and will seal the inflatable body, and turning the stem a second direction will allow the air to escape and will deflate the inflatable body.

2. The apparatus of claim 1, wherein the main body comprises an upper end comprising cut-outs.

3. The apparatus of claim 1, wherein the main body comprises inside pins.

4. The apparatus of claim 1, wherein the main body comprises a lower end comprising a cylindrical section comprising an inside portion and the means of securing the stem to the support structure comprises mating female threads.

5. The apparatus of claim 1, wherein the means of securing the inflatable body to the support structure comprises an insert disc.

6. The apparatus of claim 5, wherein the insert disc comprises outside pins attached to the insert disc.

7. The apparatus of claim 1, wherein the stem is cylindrical and the means of securing the stem to the support structure comprises mating male threads.

8. The apparatus of claim 4, wherein the means of securing the stem to the support structure comprising the inside portion and mating female threads of the cylindrical section of the lower end of the main body.

9. A method for inflating, sealing, and deflating an inflatable body, comprising the steps of:
    a) providing an apparatus for inflating, sealing, and deflating an inflatable body comprising:
        a support structure comprising a main body and an opening;
        a stem comprising a top end, a bottom end, and a hole from the top end to the bottom end; and
        a means of securing an inflatable body to the support structure, comprising
        a means of securing the inflatable body to the stem and a means of securing the stem to the support structure, wherein the means for securing the inflatable body to the stem comprises a tighten wire, adhesive, glue, strap, or annulus;

wherein the stem is configured to inflate the inflatable body when the stem is injected with air or other gases, and further wherein turning the stem in a first direction will stop the air from escaping and will seal the inflatable body, and turning the stem in a second direction will allow the air to escape and will deflate the inflatable body;

b) attaching an inflatable body to the means of securing the inflatable body to the support structure whereby the inflatable body is stabilized comprising mounting a neck or opening portion of the inflatable body around the hole in the top end of the stem to form an air-tight seal, creating a passageway between the neck or opening portion of the inflatable body and the top end of the stem, securing the stem to the support structure, and securing the means of securing the inflatable body to the support structure to the support structure;

c) injecting air or other gases into the hole in the bottom end of the stem, whereby injecting the air or other gases into the hole passes the air or other gases into the inflatable body, thereby inflating it;

d) turning the stem in a first direction, thereby stopping the air or other gases from escaping, thereby sealing the inflatable body; and e) turning the stem a second direction, thereby allowing the air or other gases to escape, thereby deflating the inflatable body.

10. The method of claim 9, wherein the means of securing the inflatable body to the support structure comprises an insert disc to stabilize the neck or opening portion of the inflatable body.

11. The method of claim 9, wherein the stem is cylindrical and the means of securing the stem to the support structure comprises utilizing mating male threads.

12. The method of claim 9, wherein the main body comprises a lower end comprising a cylindrical section comprising an inside portion and the means of securing the stem to the support structure comprises mating female threads.

13. The method of claim 9, wherein the means of securing the inflatable body to the support structure comprises an insert disc, wherein the insert disc comprises outside pins attached to the insert disc.

* * * * *